United States Patent
Ducreux et al.

(10) Patent No.: US 8,551,900 B2
(45) Date of Patent: Oct. 8, 2013

(54) PURIFICATION OF AN OLEFINIC FRACTION BY ADSORPTION ON ALUMINA-FAUJASITE CO-GRANULES

(75) Inventors: Olivier Ducreux, Louveciennes (FR); Christophe Nedez, Salindres (FR); Catherine Pommier, Saint Julien les Rosiers (FR)

(73) Assignee: IFP Energies nouvelles, Rueil-Malmaison Cedex (FR)

( * ) Notice: Subject to any disclaimer, the term of this patent is extended or adjusted under 35 U.S.C. 154(b) by 800 days.

(21) Appl. No.: 12/667,795

(22) PCT Filed: Jun. 18, 2008

(86) PCT No.: PCT/FR2008/000852
§ 371 (c)(1),
(2), (4) Date: Jan. 5, 2010

(87) PCT Pub. No.: WO2009/010666
PCT Pub. Date: Jan. 22, 2009

(65) Prior Publication Data
US 2010/0197989 A1      Aug. 5, 2010

(30) Foreign Application Priority Data
Jul. 6, 2007 (FR) ...................................... 07 04940

(51) Int. Cl.
*B01J 29/06* (2006.01)
(52) U.S. Cl.
USPC ............... 502/64; 502/79; 502/407; 502/414; 502/415
(58) Field of Classification Search
USPC ............................. 502/64, 79, 407, 414, 415
See application file for complete search history.

(56) References Cited

U.S. PATENT DOCUMENTS

| | | | |
|---|---|---|---|
| 3,790,467 A * | 2/1974 | Fiocco et al. | 208/424 |
| 3,868,299 A * | 2/1975 | Ulisch et al. | 428/34 |
| 3,899,310 A | 8/1975 | Chi et al. | |
| 6,638,340 B1 | 10/2003 | Kanazirev et al. | |
| 2001/0049998 A1 * | 12/2001 | Rode et al. | 95/117 |
| 2002/0147377 A1 | 10/2002 | Kanazirev | |

FOREIGN PATENT DOCUMENTS

FR      2 817 772 A1      6/2002

OTHER PUBLICATIONS

International Search Report of PCT/FR2008/000852 (May 28, 2009).

* cited by examiner

*Primary Examiner* — Elizabeth Wood
(74) *Attorney, Agent, or Firm* — Millen, White, Zelano & Branigan, P.C.

(57) ABSTRACT

Method for preparation of an adsorbent that comprises successive shaping stages by co-granulation of a faujasite-type zeolite powder A, with a powder B that consists of alumina, whereby the ratio per unit of mass of the powder A in the mixture of powders A and B is between 10 and 70%, for treatment under water vapor and drying.

The invention also relates to a process for adsorption of organic contaminants that contain at least one heteroatom and that are present in an olefinic feedstock that comprises at least 50% by volume of hydrocarbons, whereby this process comprises the stage for bringing the olefinic feedstock into contact with the adsorbent that is obtained by the preparation method according to the invention.

8 Claims, No Drawings

PURIFICATION OF AN OLEFINIC FRACTION BY ADSORPTION ON ALUMINA-FAUJASITE CO-GRANULES

This invention relates to a method for preparation of an adsorbent that comprises the following successive stages:
- A co-granulation of a zeolite powder A with a powder B that consists of alumina, whereby the ratio per unit of mass of A in the mixture of powders A and B is between 10 and 70%,
- A treatment under water vapor at a temperature of between 40 and 200° C. for a duration of 1 to 24 hours,
- A drying stage at a temperature of between 100 and 300° C. for a duration of 0.5 to 12 hours,
- Optionally, a stage D for calcination of the adsorbent at a temperature that is between 200 and 700° C.

This invention also relates to a process for adsorption of organic contaminants that contain at least one heteroatom. These contaminants are generally present in an olefinic feedstock that comprises at least 50% by volume of hydrocarbons. The process generally comprises the stage for bringing said olefinic feedstock into contact with an adsorbent that is obtained by the preparation method according to the invention.

Prior Art

The prior art describes the methods for preparation of faujasite-alumina co-granules.

There are already processes for preparation with an agglomerant for A-type and faujasite-type zeolites that are based on the preparation of the reaction material by mixing an aqueous sodium silicate solution with an aqueous sodium aluminate solution and formation, in this case, of a sol that coagulates spontaneously in gel, whereby the latter is then subjected to crystallization. In this case, a finely dispersed crystalline zeolite is formed that, after crystallization, is to be separated from the mother liquor, washed with water, and subjected to forming with the addition of an agglomerant in granule form, and finally dried and calcined (see, for example, the patents U.S. Pat. Nos. 2,882,243 and 3,234,147).

There are also processes for preparation without synthetic zeolite agglomerants in granule form. Such processes consist in preparing reaction materials such as aluminosilicate alkaline pastes that are transformed into granules. They are then subjected to crystallization. After crystallization, the granules are washed with water, and they are dried (see, for example, the patent U.S. Pat. No. 3,094,383).

The method for preparation of the adsorbent according to the invention, however, leads to performance levels of purification by adsorption that are clearly superior to the one that is obtained in the prior art.

DETAILED DESCRIPTION OF THE INVENTION

The invention therefore relates to a method for preparation of an adsorbent that comprises the following successive stages:
- A) A stage A for shaping a faujasite-type zeolite powder A by co-granulation with a powder B that consists of alumina, whereby the ratio per unit of mass of the powder A in the mixture of powders A and B is between 10 and 70%, preferably between 15 and 60%, very preferably between 20 and 60%, more preferably between 21 and 57%, even more preferably between 35 and 57%, even more preferably between 40 and 57%, and even still more preferably between 45 and 55%.
- B) A stage B for treatment under water vapor of the adsorbent that is obtained at the end of stage A at a temperature of between 40 and 200° C., preferably between 50 and 160° C., very preferably between 60 and 120° C., for a duration of 30 minutes to 24 hours, preferably 1 to 12 hours, very preferably from 2 to 11 hours, and very preferably from 3 to 7 hours.
- C) A stage C for drying the adsorbent that is obtained at the end of stage B at a temperature of between 100 and 300° C., preferably between 150 and 250° C., very preferably between 190 and 210° C., and for a duration of 0.5 to 12 hours, preferably from 1 to 10 hours, very preferably from 1 to 4 hours, very preferably from 1 to 3 hours, and more preferably from 1.5 to 2.5 hours.

Within the scope of the invention, adsorbent or co-granules will be mentioned for referring to the same solid.

A mixture of the two powders A and B is generally made before shaping the unit. It is preferably carried out by means of a rotary technology known by one skilled in the art, such as, for example, granulation in a holding plate or in a drum.

Optionally, drying stage C is followed by a stage D for calcination of the adsorbent at a temperature that is between 200 and 700° C., preferably between 250 and 600° C., and even preferably between 250 and 500° C. The duration of the calcination stage D is generally between 1 and 7 hours, and preferably between 1 and 5 hours.

Generally, the faujasite-type zeolite is an NaX zeolite.

According to a preferred variant, the powder B is obtained by the process that is known by one skilled in the art for quick dehydration of an alumina hydroxide, preferably hydrargillite.

Generally, the adsorbent is doped by one or more elements that are selected from the groups that consist of:
- Alkaline oxides
- Alkaline-earth oxides,
- Rare earth oxides.

The content by mass of the adsorbent of oxides of doping elements corresponds by definition to the total content by mass of oxides of doping elements from which is removed the content by mass of sodium oxide provided by the powder A, and it is generally less than 20%, preferably less than 10%, and advantageously between 500 ppm and 5%.

The dopants are generally added by dry impregnation of the powder A or the powder B, or the powder A and the powder B before shaping stage A or by dry impregnation of the adsorbent during or at the end of stage A.

According to a preferred method, the dopants are added to at least one of the two powders that are used before initiating the shaping stage A.

The invention also relates to the adsorbent that is obtained by stages A, B and C or A, B, C and D of the preparation process according to the invention. The specific surface area of said adsorbent is generally between 300 and 900 m$^2$/g, preferably between 300 and 600 m$^2$/g, preferably between 320 and 580 m$^2$/g, and even between 350 and 550 m$^2$/g. The adsorbent generally comes in all of the usual forms that are known by one skilled in the art, such as, for example, powder, balls, extrudates, in crushed form, and monoliths. Preferably, the adsorbent is shaped in the form of balls during stage A. The size of the balls is then generally between 0.5 and 10 mm inclusive, preferably between 0.7 and 8 mm inclusive, and even preferably between 0.8 and 5 mm inclusive.

The invention also relates to a process for adsorption of organic contaminants that contain at least one heteroatom and that are present in an olefinic feedstock that comprises at least 50% by volume of hydrocarbons, preferably 60% by volume of hydrocarbons, and even 70% by volume of hydrocarbons, and even 80% by volume of hydrocarbons. This process comprises the stage for bringing said olefinic feedstock into contact with the adsorbent that is obtained by one of the preparation methods according to the invention, whereby this contact is carried out preferably under dynamic conditions, whereby the adsorbent is generally arranged in a fixed bed. The olefinic feedstock generally comprises hydrocarbons that comprise 2 to 12 carbon atoms and more particularly 3 to 10 carbon atoms and more especially 3 to 7 carbon atoms. The olefinic feedstock generally originates from a steam-cracking device or a fluidized catalytic cracking, and the overall volumetric content of olefins in the feedstock is generally between 20 and 100%, preferably between 40 and 80% of olefins, and more preferably between 40 and 60%.

The organic contaminants generally comprise at least one compound that comprises at least one heteroatom that is selected from the group that consists of nitrogen, sulfur and oxygen. The organic contaminants generally comprise at least one compound that is selected from the group that consists of nitriles, pyrrole, dimethylformamide, aniline, methyl mercaptan, ethyl mercaptan, propyl mercaptan, sulfur compounds, thiophene, ketones, aldehydes, ethers, and alcohols, preferably at least one compound that is selected from the group that consists of acetonitrile, dimethylformamide, acetone, aniline, methyl mercaptan, and methanol.

Generally, the nitriles correspond to acetonitrile and to propionitrile. Generally, the light mercaptans correspond to methyl mercaptan, to ethyl mercaptan, and even to propyl mercaptan. Generally, the sulfur compounds correspond to $H_2S$, $COS$, $CS_2$, dimethyl disulfide DMDS or diethyl disulfide DEDS. Generally, the ketones correspond to acetone. Generally, the aldehydes correspond to acetaldehyde. Generally, the ethers correspond to MTBE, and to ETBE. Generally, the alcohols correspond to methanol or to ethanol. The organic contaminants generally comprise any of these molecules, or a mixture of several of these molecules.

Generally, the prepared co-granules can be used in continuous or intermittent industrial processes (batch processes, for example), optionally with a regeneration stage. The TSA (Temperature Swing Adsorption according to the English terminology) temperature-modulated adsorption process is generally used.

The content by mass of the adsorbent of doping element oxides (here, content by mass of $Na_2O$) corresponds to the total content by mass of doping element oxides from which is removed the content by mass of sodium oxide provided by the powder A.

The solids D to G are prepared by co-granulation, in a holding plate, of an NaX zeolite powder (powder A) and a powder B, resulting from the dehydration of hydrargillite, in various proportions indicated in Table I.

After shaping, a treatment under water vapor is carried out at 100° C. for 6 hours, before drying that is carried out at 200° C. for 2 hours and calcination at 400° C. for 2 hours.

The solid C is obtained by simple granulation of the powder B; the same subsequent heat treatments as those described in cases D to G are followed.

The solid H results from so-called dry impregnation of soda that is carried out on the previously obtained balls E. Drying is then conducted for 2 hours at 200° C., followed by a calcination at 400° C. for 2 hours.

Example 2

Adsorption experiments were conducted in a liquid medium. The study was carried out on 1 gram of adsorbent, previously regenerated under a stream of nitrogen at 300° C. for 2 hours, and then placed in a glass Erlenmeyer flask that contains 300 ml of 1-dodecene with a determined concentration of a selected impurity.

The Erlenmeyer flask is sealed hermetically by a lapped glass plug so as to prevent any parasitic evaporation, and it is kept at the desired temperature by means of a water bath.

The reduction of the impurity concentration of the organic solution is followed by UV-visible or by gas-phase chromatography and makes it possible to determine the uptake of mass of the adsorbent of the impurity being considered.

The results that are obtained are indicated in Tables II and III. They illustrate the advantage of using the adsorbents E, F and G according to the invention relative to the adsorbents C, D and G according to the prior art. Actually, the adsorbents according to the invention pick up the organic contaminants better.

EXAMPLES

Example 1

TABLE I

Characteristics of the Studied Adsorbents

|  | Adsorbents | | | | | |
|---|---|---|---|---|---|---|
| Characteristics | C | D | E | F | G | H |
| Shape | Balls | Balls | Balls | Balls | Balls | Balls |
| A (% by Weight) | 0 | 5 | 30 | 50 | 85 | 30 |
| B (% by Weight) | 100 | 95 | 70 | 50 | 15 | 70 |
| Diameter (mm) | 2-5 | 2-5 | 2-5 | 2-5 | 2-5 | 2-5 |
| Specific Surface Area ($m^2/g$) | 342 | 359 | 424 | 454 | 609 | 339 |
| Total Pore Volume (ml/100 g) | 44.3 | 45.7 | 51.3 | 62.15 | 71.4 | 47.0 |
| Content by Mass of $Na_2O$ (% by Weight) | 0.35 | 0.33 | 0.25 | 0.18 | 0.05 | 2.15 |

TABLE II

Uptake of mass (in %) observed per 1 gram of adsorbent exposed to a 300 ml solution of 1-dodecene, letting in 400 ppm of aniline, based on the reaction time and the temperature of the medium

|  | Adsorbents | | | | | |
|---|---|---|---|---|---|---|
| Conditions | C | D | E | F | G | H |
| 400 ppm of Aniline, 30 hours at 25° C. | 4.4 | 4.4 | 8.7 | 11.1 | 3.9 | 9.8 |
| 400 ppm of Aniline, 30 hours at 35° C. | 3.8 | 3.9 | 7.4 | 9.8 | 3.0 | 8.5 |
| 400 ppm of Aniline, 3 hours at 45° C. | 2.4 | 2.5 | 4.9 | 6.1 | 1.8 | 5.5 |
| 400 ppm of Aniline, 30 hours at 45° C. | 3.6 | 3.8 | 5.6 | 6.9 | 2.5 | 6.4 |

TABLE III

Uptake of mass (in %) observed per 1 gram of adsorbent exposed to a 300 ml solution of 1-dodecene, letting in 200 ppm of dimethylformamide (DMF) or 200 ppm of acetonitrile, after 30 hours of reaction at 25° C.

|  | Adsorbents | | | | | |
|---|---|---|---|---|---|---|
| Conditions | C | D | E | F | G | H |
| 200 ppm of DMF, 30 hours at 25° C. | 2.9 | 3.2 | 5.4 | 6.8 | 3.5 | 5.8 |
| 200 ppm of Acetonitrile, 30 hours at 25° C. | 1.9 | 1.7 | 3.7 | 4.8 | 2.4 | 4.3 |

The invention claimed is:

1. A method for preparation of an adsorbent that comprises the following successive stages:
   A) A stage A shaping a faujasite-type zeolite powder A by co-granulation with a powder B that consists essentially of alumina, whereby the ratio per unit of mass of the powder A in the mixture of powders A and B is between 10 and 70%,
   B) A stage B treating under water vapor of the adsorbent that is obtained at the end of stage A at a temperature of between 40 and 200° C., for a duration of 1 to 12 hours,
   C) A stage C drying the adsorbent that is obtained at the end of stage B at a temperature of between 100 and 300° C. for a duration of 0.5 to 12 hours,
   whereby the resultant absorbent is suitable for absorbing organic contaminants that contain at least one heteroatom and that are present in an olefinic feedstock that comprises at least 50% by volume of hydrocarbons, said hydrocarbons comprising 2 to 12 carbon atoms.

2. The preparation method according to claim 1, in which the drying stage C is followed by a stage D calcining of the adsorbent at a temperature that is between 200 and 700° C.

3. The preparation method according to claim 1, in which the faujasite-type zeolite is an NaX zeolite.

4. The preparation method according to claim 1, in which the stage B is carried out at a temperature of between 50 and 160° C. for a duration of 2 to 11 hours and in which the stage C is carried out at a temperature of between 150 and 250° C. for a duration of 1 to 10 hours.

5. The preparation method according to claim 1, in which the adsorbent is doped by one or more alkaline oxides, alkaline-earth oxides, or rare earth oxides.

6. The preparation method according to claim 5, in which the content by mass of doping elements is less than 20% of the adsorbent in oxides.

7. The preparation method according to claim 5, in which the dopants are added by dry impregnation of the powder A or of the powder B, or powder A and powder B before the shaping stage A or by dry impregnation of the adsorbent during stage A or following stage A.

8. The preparation method according to claim 1, in which the adsorbent is shaped in the form of balls during stage A.

* * * * *

UNITED STATES PATENT AND TRADEMARK OFFICE
CERTIFICATE OF CORRECTION

PATENT NO. : 8,551,900 B2
APPLICATION NO. : 12/667795
DATED : October 8, 2013
INVENTOR(S) : Ducreux et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 801 days.

Signed and Sealed this

Fifteenth Day of September, 2015

Michelle K. Lee
*Director of the United States Patent and Trademark Office*